United States Patent
Ward et al.

(10) Patent No.: US 9,352,100 B2
(45) Date of Patent: May 31, 2016

(54) NEEDLE SAFETY DEVICE

(71) Applicants: Chris Ward, Prestatyn (GB); John Slemmen, Merseyside (GB)

(72) Inventors: Chris Ward, Prestatyn (GB); John Slemmen, Merseyside (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 77 days.

(21) Appl. No.: 14/346,645

(22) PCT Filed: Sep. 20, 2012

(86) PCT No.: PCT/EP2012/068569
§ 371 (c)(1),
(2) Date: Mar. 21, 2014

(87) PCT Pub. No.: WO2013/041640
PCT Pub. Date: Mar. 28, 2013

(65) Prior Publication Data
US 2014/0236100 A1    Aug. 21, 2014

(30) Foreign Application Priority Data
Sep. 23, 2011    (EP) .................................. 11182629

(51) Int. Cl.
*A61M 5/32* (2006.01)
*A61M 5/34* (2006.01)

(52) U.S. Cl.
CPC ............. *A61M 5/3204* (2013.01); *A61M 5/326* (2013.01); *A61M 5/3272* (2013.01); *A61M 2005/325* (2013.01); *A61M 2005/3267* (2013.01); *A61M 2005/342* (2013.01)

(58) Field of Classification Search
CPC .......................... A61M 5/3272; A61M 5/3271
USPC .................................................. 604/192–198
See application file for complete search history.

(56) References Cited

U.S. PATENT DOCUMENTS

| | | | | |
|---|---|---|---|---|
| 5,984,899 A | * | 11/1999 | D'Alessio | A61M 5/3271 604/192 |
| 6,884,237 B2 | * | 4/2005 | Asbaghi | 604/198 |
| 2003/0144630 A1 | * | 7/2003 | Chang et al. | 604/198 |
| 2004/0111064 A1 | * | 6/2004 | Asbaghi | A61M 5/3272 604/198 |
| 2004/0230158 A1 | * | 11/2004 | Malenchek | 604/110 |
| 2009/0259178 A1 | | 10/2009 | Brechbuehler et al. | |
| 2010/0268170 A1 | * | 10/2010 | Carrel et al. | 604/198 |
| 2011/0082428 A1 | * | 4/2011 | Huang | 604/198 |
| 2011/0118667 A1 | * | 5/2011 | Zaiken | A61M 5/3202 604/138 |
| 2011/0319833 A1 | * | 12/2011 | Chun | 604/198 |

FOREIGN PATENT DOCUMENTS

| | | |
|---|---|---|
| DE | 29721448 U1 | 2/1998 |
| DE | 20103440 U1 | 7/2001 |
| WO | 2007099367 A1 | 9/2007 |

* cited by examiner

*Primary Examiner* — Gerald Landry, II
(74) *Attorney, Agent, or Firm* — Fish & Richardson P.C.

(57) ABSTRACT

Described is a needle safety device comprising a needle hub having a radial protrusion, a needle coupled to the needle hub and having a distal tip, and an inner sleeve telescopically coupled to the needle hub. The inner sleeve includes a first track adapted to engage the radial protrusion. The first track includes an axial section and a radial section. When the inner sleeve is in a first advanced position (PA1) and a first angular position (P1) relative to the needle hub, the radial protrusion is engaged in the first track and the distal tip is covered. When the inner sleeve is in a retracted position (PR) relative to the needle hub, the radial protrusion is in the axial section and the distal tip is exposed. When the inner sleeve is in a second advanced position (PA2) relative to the needle hub and a second angular position (P2), the radial protrusion is in the radial section and the distal tip is covered.

11 Claims, 5 Drawing Sheets

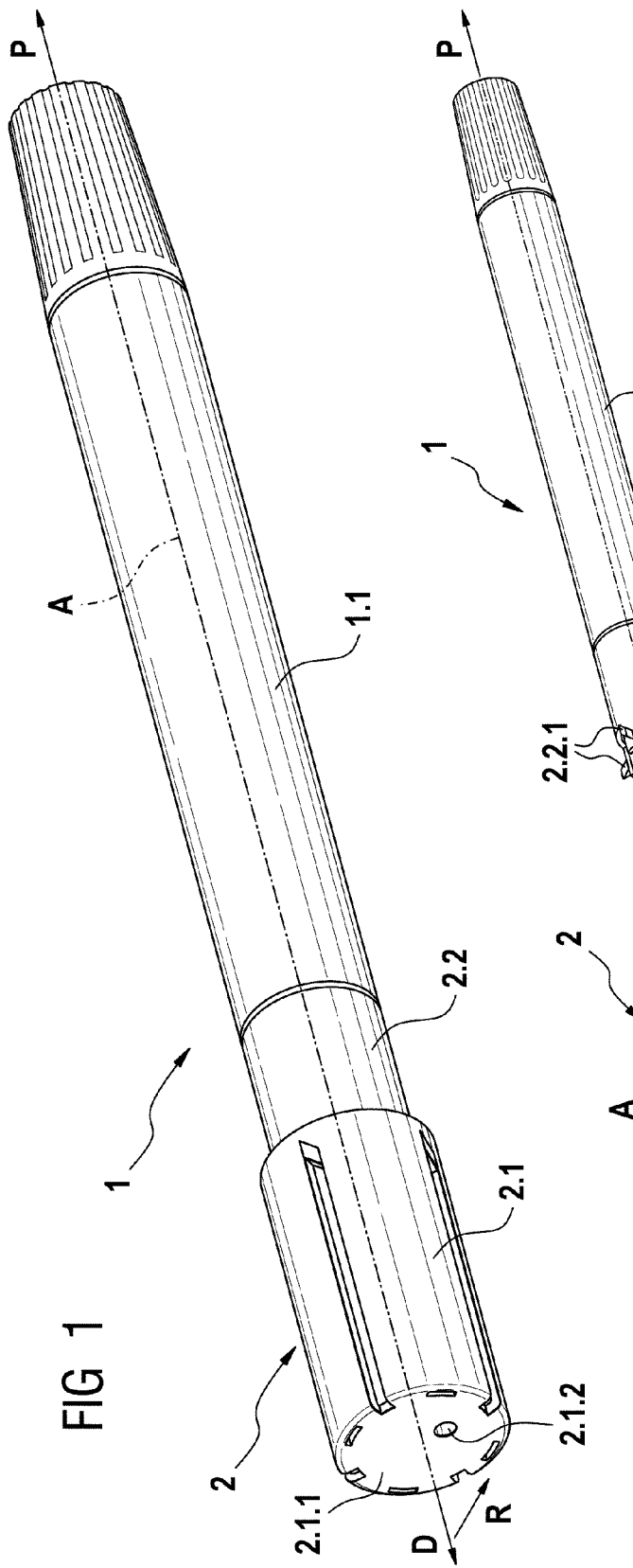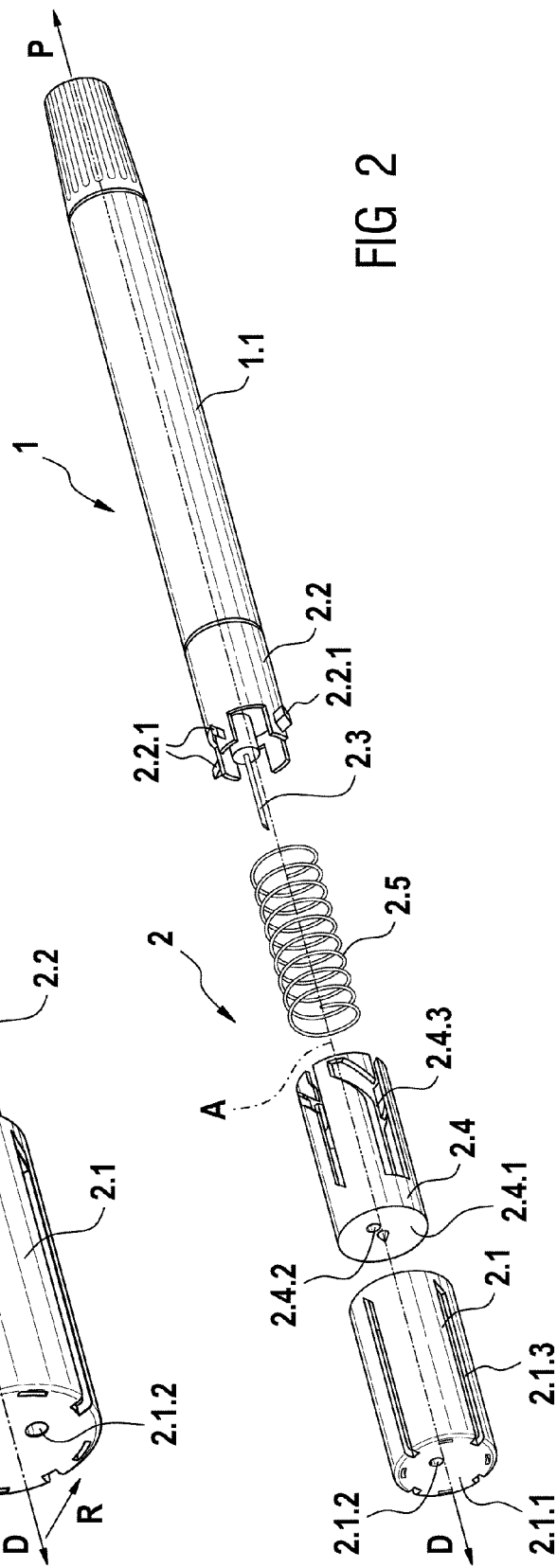

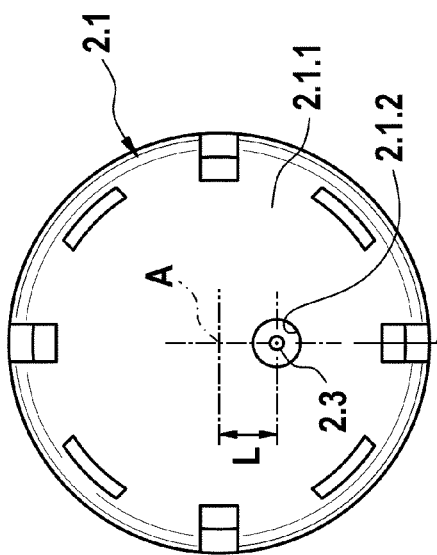
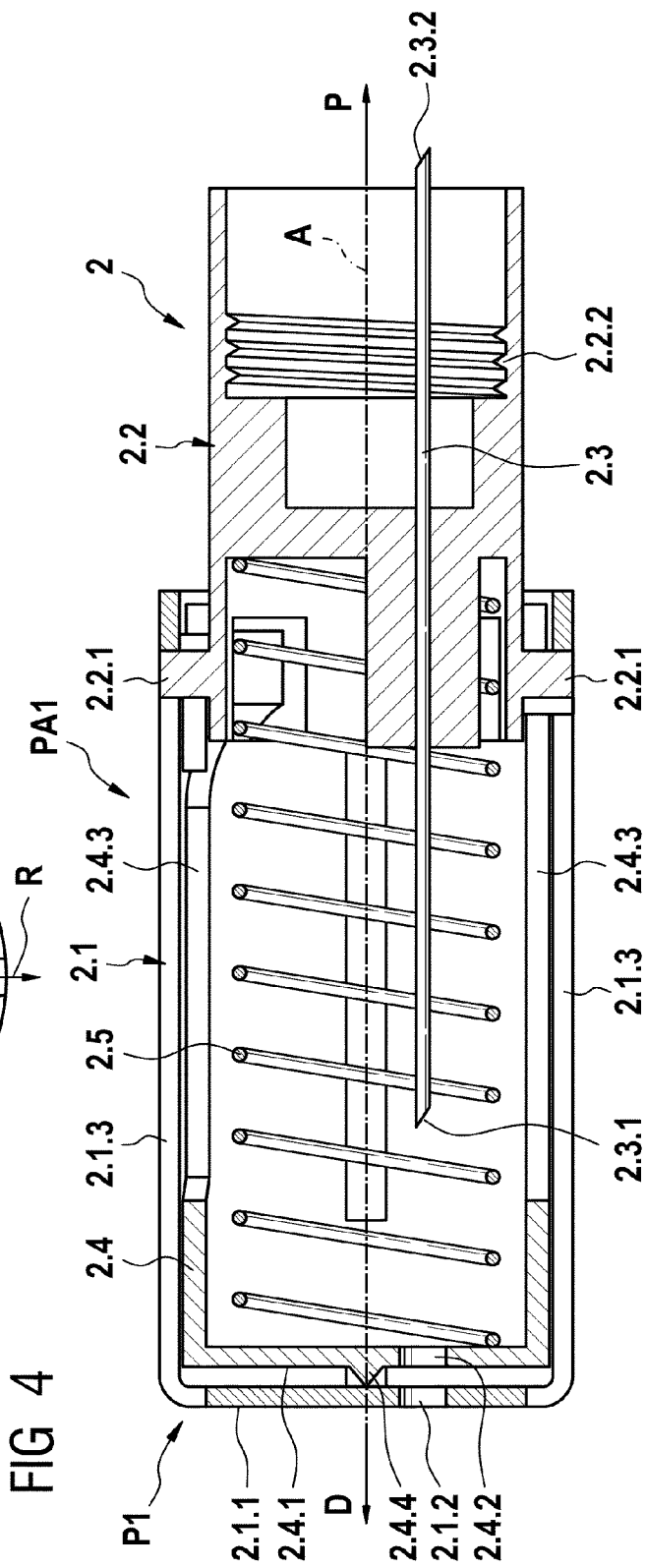

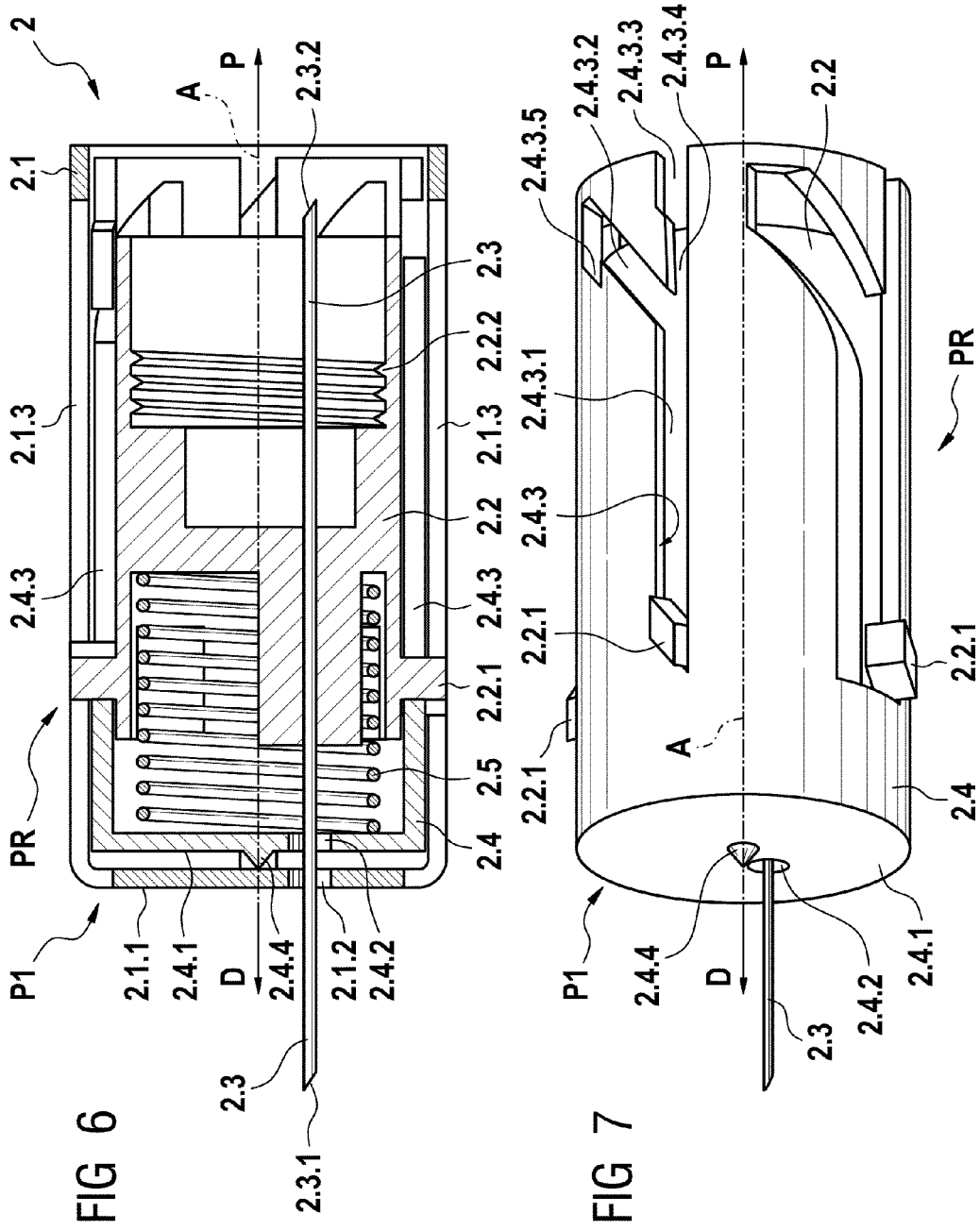

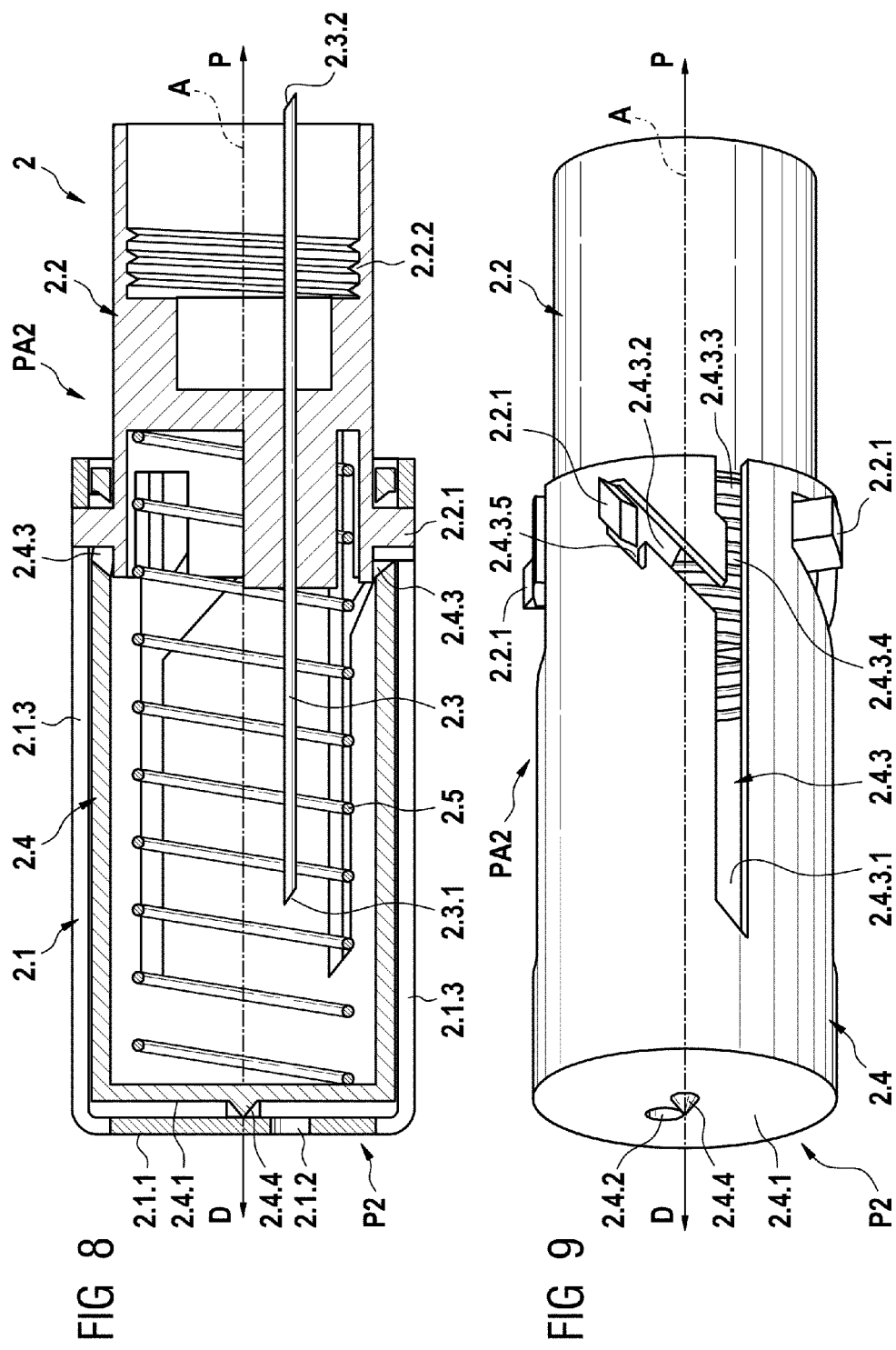

NEEDLE SAFETY DEVICE

CROSS REFERENCE TO RELATED APPLICATIONS

The present application is a U.S. National Phase Application pursuant to 35 U.S.C. §371 of International Application No. PCT/EP2012/068569 filed Sep. 20, 2012, which claims priority to European Patent Application No. 11182629.3 filed Sep. 23, 2011. The entire disclosure contents of these applications are herewith incorporated by reference into the present application.

FIELD OF INVENTION

It is an object of the present invention to provide an improved safety needle assembly that minimizes the risk of an accidental needle stick injury, that is safe to handle, and that provides needle safety before and after the medicament is delivered.

BACKGROUND

Medicament delivery devices (e.g., pen injectors, syringes, auto-injectors, etc.) that contain a selected dosage of a medicament are well known devices for administering the medicament to a patient. Safety devices for covering a needle of the delivery device before and after use are also well known. Typically, a needle shield of the safety device is either manually moved or automatically to surround the medical needle. Various attempts have been made to develop an optimally sized and functioning safety device. However, there remains a need for an optimal safety needle assembly.

SUMMARY

In an exemplary embodiment, a needle safety device comprises a needle hub having a radial protrusion, a needle coupled to the needle hub and having a distal tip, and an inner sleeve telescopically coupled to the needle hub. The inner sleeve includes a first track adapted to engage the radial protrusion. The first track includes an axial section and a radial section. When the inner sleeve is in a first advanced position and a first angular position relative to the needle hub, the radial protrusion is engaged in the first track and the distal tip is covered. When the inner sleeve is in a retracted position relative to the needle hub, the radial protrusion is in the axial section and the distal tip is exposed. When the inner sleeve is in a second advanced position relative to the needle hub and a second angular position, the radial protrusion is in the radial section and the distal tip is covered.

In an exemplary embodiment, the radial protrusion includes a proximal ramped surface and a distal ramped surface.

In an exemplary embodiment, the first track includes an engagement section adapted to deflect when the radial protrusion engages the first track and prevent disengagement of the inner sleeve from the needle hub when engaged. A width of the engagement section is less than a width of the radial protrusion.

In an exemplary embodiment, the first track includes a locking section adapted to engage the radial protrusion when a proximally directed force is applied to the inner sleeve when the inner sleeve is in the second advanced position and the second angular position.

In an exemplary embodiment, the needle safety device further comprises a spring biasing the inner sleeve in a distal direction.

In an exemplary embodiment, the needle safety device further comprises a needle shield rotatably coupled to the inner sleeve. The needle shield has a first aperture. The needle shield includes a second track adapted to engage the radial protrusion. The inner sleeve includes a second aperture. In the first angular position the first aperture is aligned with the second aperture and in the second angular position, the first aperture is not aligned with the second aperture.

In an exemplary embodiment, the needle is disposed in an axis parallel to and offset from a longitudinal axis A of the needle safety device.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 shows an isometric view of an exemplary embodiment of a needle safety device mounted to an injection device.

FIG. 2 shows an exploded view of an exemplary embodiment of a needle safety device and an injection device.

FIG. 3 shows a top view of an exemplary embodiment of a first base member of a needle shield.

FIG. 4 shows a sectional view of an exemplary embodiment of a needle safety device having a needle shield and a needle assembly.

FIG. 6 shows a sectional view of an exemplary embodiment of a needle safety device arranged in a retracted position.

FIG. 7 illustrates an exemplary embodiment of a needle safety device arranged in a retracted position in an isometric view.

FIG. 8 shows a sectional view of an exemplary embodiment of a needle safety device arranged in a second advanced position.

FIG. 9 illustrates an exemplary embodiment of a needle safety device arranged in a second advanced position in an isometric view.

Corresponding parts are marked with the same reference symbols in all figures.

DETAILED DESCRIPTION

Figure 5:
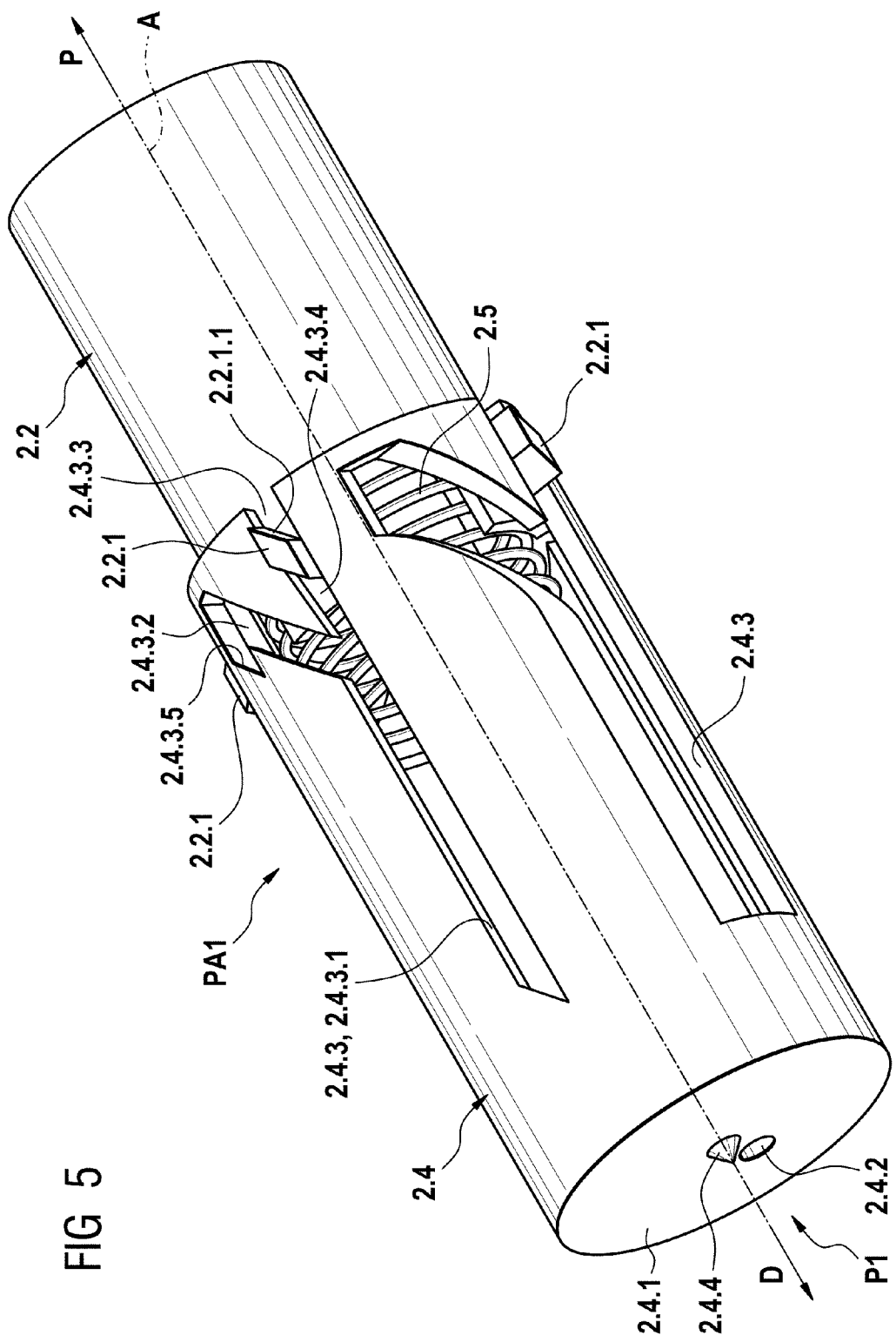
FIG. 5 illustrates an exemplary embodiment of a needle safety device arranged in a first advanced position in an isometric view.

FIGS. 1 and 2 show an exemplary embodiment of a medicament delivery assembly including an injection device 1 and a needle safety device 2. The injection device 1 may be any type of delivery device including, but not limited to a syringe, a pen injector, an auto-injector, etc. In an exemplary embodiment, the injection device 1 may have a housing 1.1 that is cylindrical for gripping when administering an injection. The injection device 1 may be disposable after a single use or after a container of medicament in the housing 1.1 has been emptied. The injection device 1 may be reusable, and the container may be replaced when empty. The needle safety device 2 may be coupled, removably or irremovably, to a distal end of the injection device 1.

FIG. 2 shows an exemplary embodiment of components of the needle safety device 2. In an exemplary embodiment, a needle hub 2.2 is coupled to the injection device 1. The needle hub 2.2 may be removably coupled to the injection device 1 (e.g., by a threaded coupling, snap fit, bayonet fit, friction fit, etc.) or formed integrally with the injection device 1. A needle 2.3 may be removably coupled to the needle hub 2.2 or integrally formed or adhered to the needle hub 2.2.

An inner sleeve 2.4 may be telescopically coupled to the needle hub 2.2 and a needle shield 2.1 may be coupled to the inner sleeve 2.4.

FIGS. 3 and 4 show an exemplary embodiment of a needle safety device 2 according to the present invention. In an exemplary embodiment, the needle hub 2.2 may include a thread 2.2.2 for mating with a corresponding thread on the injection device 1. The needle hub 2.2 may include the needle 2.3 which includes a proximal tip 2.3.2 for piercing a septum of a container of medicament in the injection device 1 and a distal tip 2.3.1 for piercing skin of the patient. In an exemplary embodiment, a longitudinal axis A of the needle hub 2.2 may be aligned with a longitudinal axis of the injection device 1, and the needle 2.3 may lie in an axis parallel to and offset from the axis A. In another exemplary embodiment, the needle 2.3 may lie on the axis A.

The spring 2.5 may be grounded proximally on a portion of the needle hub 2.2 and distally on a proximal surface of a distal face 2.4.1 of the inner sleeve 2.4. The spring 2.5 may bias the inner sleeve 2.4 in a first advance position (PA1) relative to the needle hub 2.2.

The inner sleeve 2.4 may maintain engagement with the needle hub 2.2 by engaging a radial projection formed on the needle hub 2.2. The inner sleeve 2.4 includes a second aperture 2.4.2 for allowing the needle 2.3 to pass through when the needle safety device 1 is pressed against an injection site.

In an exemplary embodiment, the needle shield 2.1 fits over the inner sleeve 2.4. The needle shield 2.1 may be rotatable relative to the inner sleeve 2.4. The needle shield 2.1 includes a first aperture 2.1.2, aligned with the second aperture 2.4.2 on the inner sleeve 2.4, for allowing the needle 2.3 to pass through when the needle safety device 1 is pressed against an injection site.

FIG. 5 shows an exemplary embodiment of the needle hub 2.2 and the inner sleeve 2.4 according to the present invention. In the exemplary embodiment shown in FIG. 5, the inner sleeve 2.4 is in the first advanced position (PA1) and a first angular position (P1). The inner sleeve 2.4 may engage the needle hub 2.2 when the radial protrusion 2.2.1 on the needle hub 2.2 is inserted into a first track 2.4.3 formed in the inner sleeve 2.4. In an exemplary embodiment, the first track 2.4.3 includes an engagement section 2.4.3.4 adapted to retain the radial protrusion 2.2.1. The engagement section 2.4.3.4 may include an inlet portion 2.4.3.3 having a ramped surface which engages a distal ramped surface on the radial protrusion 2.2.1 and causes the engagement section 2.4.3.4 to deflect allowing the radial protrusion 2.2.1 to move distally into an axial section 2.4.3.1 of the first rack 2.4.3. After the radial protrusion 2.2.1 enters the axial section 2.4.3.1, the engagement section 2.4.3.4 may return to its original position and act as a backstop, preventing the radial protrusion 2.2.1 from disengaging the first track 2.4.3. For example, the engagement section 2.4.3.4 may have a width less than a width of the radial protrusion 2.2.1.

In an exemplary embodiment, the axial section 2.4.3.1 is a formed along an axis of the inner sleeve 2.4 parallel to the axis A. The axial section 2.4.3.1 may extend a sufficient length along the inner sleeve 2.4 such that when the needle safety device 2 is pressed against the injection site, the distal tip 2.3.1 of the needle 2.3 is exposed. A radial section 2.4.3.2 of the first track 2.4.3 may intersect with the axial section 2.4.3.1, formed at an angle to the axial section 2.4.3.1 and adjacent the engagement section 2.4.3.4. As explained further below, a proximal ramped surface 2.2.1.1 on the radial protrusion 2.2.1 may abut the engagement section 2.4.3.4 and be forced into the radial section 2.4.3.2 after the needle safety device 2 is removed from the injection site.

A locking section 2.4.3.5 may be formed adjacent a proximal portion of the radial section 2.4.3.2. The radial protrusion 2.2.1 may engage the locking section 2.4.3.5 to prevent proximal movement of the needle shield 2.1 after use.

Referring back to FIG. 2, the needle shield 2.1 includes a second track 2.1.3 which is engaged by the radial protrusion 2.2.1. The second track 2.1.3 is a formed along an axis of the needle shield 2.1 parallel to the axis A. The second track 2.1.3 may extend a sufficient length along the needle shield 2.1 such that when the needle safety device 2 is pressed against the injection site, the distal tip 2.3.1 of the needle 2.3 is exposed. In an exemplary embodiment, a spacer element 2.4.4 may be formed on the distal face 2.4.1 of the inner sleeve 2.4 to abut a distal face 2.1.1 of the needle shield 2.1 to maintain axial space between the needle shield 2.1 and the inner sleeve 2.4.

FIGS. 6 and 7 show an exemplary embodiment of the needle safety device 2 in a retracted position (PR) in which the distal tip 2.3.1 of the needle 2.3 is exposed. When a proximally directed force is applied to the needle safety device 2 (e.g., during an injection procedure when the needle safety device 2 is pressed against the injection site), the needle shield 2.1 abuts the spacer element 4.4 causing the needle shield 2.1 and the inner sleeve 2.4 to move proximally relative to the needle hub 2.2 into the retracted position (PR). When moving from the first advanced position (PA1) to the refracted position (PR), the needle shield 2.1 and the inner sleeve 2.4 move axially relative to the needle hub 2.2, and the needle shield 2.1 and the inner sleeve 2.4 do not rotate relative to each other or the needle hub 2.2 (because the radial protrusion 2.2.1 is in the first and second tracks 2.1.3, 2.4.3).

When the force is removed from the needle safety device 2 (e.g., when the needle safety device 2 is removed from the injection site), the spring 2.5 applies a distally directed force to the inner sleeve 2.4 which moves the inner sleeve 2.4 and the needle shield 2.1 distally relative to the needle hub 2.2.

FIGS. 8 and 9 show an exemplary embodiment of the needle safety device 2 in a second axial position (PA2) in which the distal tip 2.3.1 of the needle 2.3 is covered by the needle shield 2.1 (and optionally, the inner sleeve 2.4). In the second axial position (PA2), the inner sleeve 2.4 may be in a second angular position (P2). As the inner sleeve 2.4 moves distally relative to the needle hub 2.2, the radial protrusion 2.2.1 moves from the axial section 2.4.3.1 of the first track 2.4.3, abuts the engagement section 2.4.3.4, and moves into the axial section 2.4.3.1. When the radial protrusion 2.2.1 moves into the axial section 2.4.3.1, the needle shield 2.1 rotates relative to the inner sleeve 2.4 into the second angular position (P2), which results in the misalignment of the first and second apertures 2.1.2, 2.4.2. Thus, if a proximally directed force is applied to the needle shield 2.1, the radial protrusion 2.2.1 will engage the locking section 2.4.3.5 of the first track 2.4.3 and the distal tip 2.3.1 will abut the distal face 2.4.1 of the inner sleeve 2.4 or the distal face 2.1.1 of the needle shield 2.1, preventing exposure of the distal tip 2.3.1.

A removable film may be disposed on the distal face 2.1.1 of the needle shield 2.1, e.g., to maintain sterility of the needle 2.3.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle safety device comprising:
   a needle hub having a radial protrusion;
   a needle coupled to the needle hub, the needle including a distal tip;
   an inner sleeve telescopically coupled to the needle hub, the inner sleeve including a first track adapted to engage the radial protrusion, the first track including an axial section and a radial section; and
   a needle shield fitting over the inner sleeve and coupled to the inner sleeve in a manner such that the needle shield is rotatable relative to the inner sleeve,
   wherein, when the inner sleeve is in a first advanced position (PA1) and a first angular position (P1) relative to the needle hub, the radial protrusion is engaged in the first track and the distal tip is covered,
   wherein, when the inner sleeve is in a retracted position (PR) relative to the needle hub, the radial protrusion is in the axial section and the distal tip is exposed, and
   wherein, when the inner sleeve is in a second advanced position (PA2) relative to the needle hub and a second angular position (P2), the radial protrusion is in the radial section and the distal tip is covered.

2. The needle safety device according to claim 1, wherein the radial protrusion includes a proximal ramped surface and a distal ramped surface.

3. The needle safety device according to claim 1, wherein the first track includes an engagement section adapted to deflect when the radial protrusion engages the first track and prevent disengagement of the inner sleeve from the needle hub when engaged.

4. The needle safety device according to claim 3, wherein a width of the engagement section is less than a width of the radial protrusion.

5. The needle safety device according to claim 1, wherein the first track includes a locking section adapted to engage the radial protrusion when a proximally directed force is applied to the inner sleeve when the inner sleeve is in the second advanced position (PA2) and the second angular position (P2).

6. The needle safety device according to claim 1, further comprising:
   a spring biasing the inner sleeve in a distal direction.

7. The needle safety device according to claim 1, wherein the needle shield has a first aperture.

8. The needle safety device according to claim 7, wherein the needle shield includes a second track adapted to engage the radial protrusion.

9. The needle safety device according to claim 7, wherein the inner sleeve includes a second aperture.

10. The needle safety device according to claim 9, wherein, in the first angular position (P1), the first aperture is aligned with the second aperture and in the second angular position (P2), the first aperture is not aligned with the second aperture.

11. The needle safety device according to claim 1, wherein the needle is disposed in an axis parallel to and offset from a longitudinal axis A of the needle safety device.

\* \* \* \* \*